US006207867B1

(12) United States Patent
Kamaya et al.

(10) Patent No.: US 6,207,867 B1
(45) Date of Patent: Mar. 27, 2001

(54) METHOD FOR PURIFYING β-PHENYLETHYL ALCOHOL

(75) Inventors: Kazuhiko Kamaya, Sodegaura; Yoshimitsu Onodera, Ichihara, both of (JP)

(73) Assignee: Sumitomo Chemical Company, Limited, Oaska (JP)

( * ) Notice: Subject to any disclaimer, the term of this patent is extended or adjusted under 35 U.S.C. 154(b) by 0 days.

(21) Appl. No.: 09/543,588

(22) Filed: Apr. 5, 2000

(30) Foreign Application Priority Data

Apr. 7, 1999 (JP) .................................................. 11-100013
Apr. 8, 1999 (JP) .................................................. 11-101231

(51) Int. Cl.⁷ .................................................. C07C 29/74
(52) U.S. Cl. .............................................................. 568/810
(58) Field of Search ............................................. 568/810

(56) References Cited

U.S. PATENT DOCUMENTS

| | | | | |
|---|---|---|---|---|
| 1,944,958 | * | 1/1934 | Valik ..................................... | 568/810 |
| 4,359,365 | * | 11/1982 | Deguchi ................................ | 568/810 |
| 4,400,558 | * | 8/1983 | Nemet-Mavrodin .................. | 568/810 |
| 4,664,755 | * | 5/1987 | Nienhaus .............................. | 568/810 |
| 5,965,780 | * | 10/1999 | Savina .................................. | 568/810 |

FOREIGN PATENT DOCUMENTS

| | | |
|---|---|---|
| 112114 | 3/1975 | (DE) . |
| 112115 | 3/1975 | (DE) . |
| 0366842B1 | 10/1993 | (EP) . |
| 2204871 | 11/1988 | (GB) . |

* cited by examiner

*Primary Examiner*—Michael L. Shippen
(74) *Attorney, Agent, or Firm*—Birch, Stewart, Kolasch & Birch, LLP

(57) ABSTRACT

A method for purifying β-phenylethyl alcohol, comprising
  an extractive distillation process in which crude β-phenylethyl alcohol is extractive-distilled using an extraction solvent (A), and
  an extracting process in which the extraction solvent (A) after use in the extractive distillation process is extracted using other extraction solvent (B).

9 Claims, No Drawings

METHOD FOR PURIFYING β-PHENYLETHYL ALCOHOL

FIELD OF THE INVENTION

The present invention relates to a method for purifying β-phenylethyl alcohol. More particularly, the present invention relates to a method for purifying β-phenylethyl alcohol having a characteristic that nasty smell components can be selectively separated and removed from crude phenylethyl alcohol efficiently by only a simple operation without requiring complicated apparatuses and operations, to obtain high purity β-phenylethyl alcohol having excellent fragrance for an aromatic and the solvent used in the process can be re-used economically.

BACKGROUND OF THE INVENTION

β-Phenylethyl alcohol is a valuable substance widely used in detergents, cosmetics and the like as a rose type aromatic, and in use thereof, products having high purity and excellent fragrance are required. In general, aromatic components degrade in commercial value even if a small amount of impurities influencing the original fragrance is present, therefore, the purification method thereof are particularly noticed. As the purification method of β-phenylethyl alcohol, there are a method in which β-phenylethyl alcohol is derived to a borate or organic acid ester for purification, a method in which impurities are adsorbed on silica gel for purification, a method of purification using higher stages purification column, as well as other methods. However, these methods have respective defects and have problems as industrial methods. Namely, the esterification method has economical disadvantages that a process for esterifying β-phenylethyl alcohol and a hydrolysis process for liberating β-phenylethyl alcohol from the ester are required, and further, an acid should be recycled, and the like. The method for adsorbing impurities has problems in that purification effect is low, and further, silica gel is recycled. In the distillation method, even if a fractionating column having higher stages is used, when components having near boiling points or azeotropic components are present, β-phenylethyl alcohol having satisfactory quality can not be obtained easily.

SUMMARY OF THE INVENTION

The present inventors have intensively studied a purification method having no problems as described above, and resultantly found that nasty smell components can be selectively separated and removed from crude β-phenylethyl alcohol efficiently by only a simple operation without requiring complicated apparatuses and operations, to obtain high purity β-phenylethyl alcohol having excellent fragrance for an aromatic, by purifying and distilling the crude β-phenylethyl alcohol with a solvent, and that the extraction solvent used for extracting the crude phenylethyl alcohol can be recycled by extracting the solvent with other solvent, and have completed the present invention.

Namely, the present invention relates to a method for purifying β-phenylethyl alcohol, comprising an extractive distillation process in which crude β-phenylethyl alcohol is extractive-distilled using an extraction solvent (A), and an extracting process in which the extraction solvent (A) after use in the extractive distillation process is extracted using other extraction solvent (B).

DETAILED DESCRIPTION OF THE PREFERRED EMBODIMENTS

As the crude β-phenylethyl alcohol which is a raw material in the present invention, those obtained by, for example, hydrogen reduction of styrene oxide, reaction of benzene with ethylene oxide, hydrogen reduction of phenylacetic acid, and oxidation reaction of an aromatic hydrocarbon compound, and the like, can be used.

Further, crude β-phenylethyl alcohol which has been washed with an alkali can also be used. As the alkaline aqueous solution, ammonia water and sodium hydroxide water are preferable, and a sodium hydroxide aqueous solution is more preferable from the standpoint of easy handling. The concentration of the alkaline aqueous solution is usually from about 1 to 50% by weight. For the washing with an alkali, it may be advantageous that crude β-phenylethyl alcohol and an alkaline aqueous solution are mixed, and then, they are separated into oil and water. The temperature in the washing is usually from room temperature (about 20° C.) to 100° C., and the amount of the alkaline aqueous solution used is preferably from 5 to 50 parts by weight based on 100 parts by weight of the crude β-phenylethyl alcohol.

The extractive distillation process in the present invention is a process in which crude -phenylethyl alcohol is extractive-distilled using an extraction solvent (A). As the extraction solvent (A), at least one solvent system selected from the group consisting of the following (I), (II) and (III) is preferable from the standpoint of removal efficiency of odor components.

(I) water.

(II) a mixture of water with 1,2-ethane diol, 1,2-propane diol or 1,3-propane diol.

(III) a mixture of water with 1,2-ethane diol monomethyl ether, 1,2-ethane diol monoethyl ether, 1,2-propane diol monomethyl ether, 1,2-propane diol monoethyl ether, 1,3-propane diol monomethyl ether or 1,3-propane diol monoethyl ether.

When the solvent system is a mixture of two or more solvents, it is preferable that the weight ratio of water to divalent alcohol or divalent alcohol monoalkyl ether is from 1:9 to 7:3. As the extractive distillation method, there is for example a method in which a raw material crude β-phenylethyl alcohol is extractive-distilled by using a mixture of extraction solvents (A), water and divalent alcohol or divalent alcohol monoalkyl ether, to distilled off extraction solvents (A) having higher volatility and impurities having nasty odor from the column top, and to extract β-phenylethyl alcohol from the column bottom. As the extractive distillation conditions, usual distillation conditions are adopted, for example, it is conducted under reduced pressure, at a temperature from 50 to 200° C. and at a refluxing ratio of 0.1 to 50. The positions for feeding crude β-phenylethyl alcohol and extracting solvent on the extractive distillation column can be controlled at will if necessary.

The extracting process in the present invention is a process in which the extraction solvent (A) after use in the extractive distillation process is extracted using other extraction solvent (B) for purification. Namely, by extracting an extraction solvent (A) containing impurities having nasty odor distilled from the extractive distillation apparatus, by using an extraction solvent (B), the extraction solvent (B) containing the impurities having nasty odor is distilled off from the column top and on the other hand, the purified extraction solvent (A) is recovered from the column bottom.

As the extraction solvent (B), hydrocarbon oils are preferable, among them, aromatic oils are preferable, further among other, aromatic hydrocarbon oils containing benzene, toluene and/or xylene are preferable, from the stand points of easy availability and efficiency for removing the impurities having nasty odor.

It is preferable to recycle the extraction solvent (A) after purification in the extracting process into the extractive distillation process, for re-use, from the standpoints of economical use of solvents, reduction in post-treatment cost after the used solvents. On the other hand, the extraction solvent (B) containing impurities having nasty odor can be purified easily, for example, known operations such as usual distillation in an aromatic plant.

The β-phenylethyl alcohol after the extractive distillation process can be made into the final product, β-phenylethyl alcohol by, for example, performing post-treatment such as distillation and the like.

According to the present invention, it is possible to provide a method for purifying β-phenylethyl alcohol in which nasty smell components can be selectively separated and removed from crude β-phenylethyl alcohol efficiently by only a simple operation without requiring complicated apparatuses and operations, to obtain high purity β-phenylethyl alcohol having excellent fragrance for an aromatic and the extraction solvent used can be re-used economically.

EXAMPLE

The following examples illustrate the present invention.

Example 1

A 62-stage extractive distillation column, a 102-stage solvent extracting column and a filled column having a height of 32 meters as a fractionating column were used, and the extractive distillation column was operated under a reduced pressure of 140 mmHg, the solvent extracting column was operated under a pressure of 240 kPa-G, and the fractionating column was operated under a reduced pressure of 200 mmHg. β-phenylethyl alcohol containing 6.5% of impurities and having nasty odor was fed to the extractive distillation column at a speed of 210 parts by weight per 1 hour, from the 23-th stage from the column top of the extractive distillation column.

On the other hand, a mixed solution of water and 1,2-propane diol (ratio by weight; 1:3), which are extraction solvents (A) recycled from the extracting process in the later stages was fed at a speed of 390 parts by weight per one hour, from the 50-th stage from the column top. In this operation, the nasty odor components were distilled at a speed of 420 parts by weight per one hour together with the mixed solution of water and 1,2-propane diol, and continuously fed to the extracting process for purification. In the extracting process, toluene, the extracting solvent (B) was fed at a speed of 150 parts by weight per one hour to the lower stages of the solvent extracting column. As a result, toluene and impurities having nasty odor were distilled off from the top of the solvent extracting column at a speed of 180 parts by weight per one hour, a mixed solution of water and 1,2-propane diol (ratio by weight; 1:3), which are extraction solvents (A) recycled from the column bottom was extracted and recycled to the extractive distillation column. On the other hand, β-phenylethyl alcohol removed out from the column bottom of the extractive distillation column was fed to the fractionating column at the site 14 m from the top, causing extraction of purified β-phenylethyl alcohol from the top of the fractionating column at a speed of 165 parts by weight per one hour. The β-phenylethyl alcohol herein obtained had a purity of 99.9% and had no nasty odor, namely qualities suitable for aromatics.

Example 2

An alkali washing bath having a rotation blade inside for improving washing efficiency was used, and operated at a temperature of 80° C. under atmospheric pressure. A 62-stage extractive distillation column, a 102-stage solvent extracting column and a filled column having a height of 32 meters as a fractionating column were used, and the extractive distillation column was operated under a reduced pressure of 80 Kp-G, the solvent extracting column was operated under a pressure of 240 kp-G, and the fractionating column was operated under a reduced pressure of 80 Kp-G. β-phenylethyl alcohol containing 21.7% of impurities and having nasty odor was fed to the alkali washing column at a speed of 278 parts by weight per 1 hour. Simultaneously, alkali water having a sodium hydroxide concentration of 25% by weight was fed at a speed of 50 parts by weight per one hour to the alkali washing bath and alkali washing was conducted.

From the 23-th stage from the top of the extractive distillation column, crude β-phenylethyl alcohol having nasty odor having a concentration of impurities changed to 17.4% by the alkali washing, was fed to the extractive distillation column at a speed of 275 parts by weight per one hour. On the other hand, a mixed solution of water and 1,2-propane diol (ratio by weight; 1:3), which are extraction solvents (A) recycled from the extracting process in the later stages was fed at a speed of 490 parts by weight per one hour, from the 40-th stage from the column top. In this operation, the nasty odor components were distilled at a speed of 560 parts by weight per one hour together with the mixed solution of water and 1,2-propane diol, and continuously fed to the extracting process for purification.

In the extracting process, toluene, the extracting solvent (B) was fed at a speed of 210 parts by weight per one hour to the lower stages of the solvent extracting column. As a result, toluene and impurities having nasty odor were distilled off from the top of the solvent extracting column at a speed of 220 parts by weight per one hour, a mixed solution of water and 1,2-propane diol (ratio by weight; 1:3), which are extraction solvents (A) purified was extracted and recycled to the extractive distillation column.

On the other hand, β-phenylethyl alcohol removed out from the column bottom of the extractive distillation column was fed to the fractionating column at the site 14 m from the top, causing extraction of purified β-phenylethyl alcohol from the top of the fractionating column at a speed of 190 parts by weight per one hour. The β-phenylethyl alcohol herein obtained had a purity of 99.5% and had no nasty odor, namely qualities suitable for aromatics.

What is claimed is:

1. A method for purifying β-phenylethyl alcohol, comprising
   an extractive distillation process in which crude β-phenylethyl alcohol is extractive-distilled using an extraction solvent (A), and
   an extracting process in which the extraction solvent (A) after use in the extractive distillation process is extracted using other extraction solvent (B).

2. The purification method according to claim 1, wherein the extraction solvent (A) is at least one solvent system selected from the group consisting of the following (I), (II) and (III):

(I) water, (II) a mixture of water with 1,2-ethane diol, 1,2-propane diol or 1,3-propane diol, (III) a mixture of water with 1,2-ethane diol monomethyl ether, 1,2-ethane diol monoethyl ether, 1,2-propane diol monomethyl ether, 1,2-propane diol monoethyl ether, 1,3-propane diol monomethyl ether or 1,3-propane diol monoethyl ether.

3. The purification method according to claim 1, wherein the extraction solvent (B) is a hydrocarbon oil.

4. The purification method according to claim 1, wherein the extraction solvent (B) is an aromatic oil.

5. The purification method according to claim 1, wherein the extraction solvent (B) is an aromatic oil containing benzene, toluene and/or xylene.

6. The purification method according to claim 1, wherein the extraction solvent (A) purified in the extracting process is recycled to the extractive distillation process.

7. The purification method according to claim 1, wherein the crude β-phenylethyl alcohol washed with an alkali aqueous solution is extractive-distilled using the extraction solvent (A).

8. The purification method according to claim 7, wherein the alkali aqueous solution is a sodium hydroxide aqueous solution.

9. The purification method according to claim 1, wherein the crude β-phenylethyl alcohol is β-phenylethyl alcohol obtained by at least one reaction selected from the group consisting of hydrogen reduction of styrene oxide, reaction of benzene with ethylene oxide, hydrogen reduction of phenylacetic acid, and oxidation reaction of an aromatic hydrocarbon compound.

* * * * *